(12) United States Patent
Lane et al.

(10) Patent No.: US 6,609,255 B2
(45) Date of Patent: Aug. 26, 2003

(54) OPTICALLY CORRECT AND CLEAR EYESHIELDS

(75) Inventors: Henry Welling Lane, San Luis Obispo, CA (US); Ronald L. Underwood, San Luis Obispo, CA (US)

(73) Assignee: Dioptics Medical Products, Inc., San Luis Obispo, CA (US)

( * ) Notice: Subject to any disclaimer, the term of this patent is extended or adjusted under 35 U.S.C. 154(b) by 16 days.

(21) Appl. No.: 10/085,168

(22) Filed: Feb. 26, 2002

(65) Prior Publication Data

US 2002/0152544 A1 Oct. 24, 2002

Related U.S. Application Data

(60) Division of application No. 09/852,406, filed on May 9, 2001, and a continuation-in-part of application No. 29/130,115, filed on Sep. 26, 2000, now Pat. No. Des. 462,374, and a continuation-in-part of application No. 29/130,173, filed on Sep. 27, 2000, now Pat. No. Des. 457,908.

(51) Int. Cl.$^7$ .................................................. A61B 9/02
(52) U.S. Cl. ............................................... 2/431; 2/436
(58) Field of Search ........................... 2/431, 436, 437, 2/439, 452, 426, 435; 351/45, 47, 156

(56) References Cited

U.S. PATENT DOCUMENTS

| D104,320 S | 4/1937 | Bouchard |
| D112,976 S | 1/1939 | Brunetti |
| D112,989 S | 1/1939 | Diodati |
| 2,300,365 A | 10/1942 | Wagner ........................... 2/14 |
| D166,578 S | 4/1952 | Splaine |
| 2,642,568 A | * 6/1953 | Stewart .......................... 2/436 |
| 2,654,090 A | * 10/1953 | Christensen et al. ........... 2/436 |
| D191,229 S | 8/1961 | Boxer .......................... D57/1 |
| D195,311 S | 5/1963 | McNeill ....................... D57/1 |
| D201,920 S | 8/1965 | McCulloch .................... D57/1 |
| 3,233,249 A | 2/1966 | Baratelli et al. ................ 2/14 |
| D204,163 S | 3/1966 | Mitchell ....................... D57/1 |
| D204,320 S | 4/1966 | Carmichael ................... D57/1 |

(List continued on next page.)

FOREIGN PATENT DOCUMENTS

| AU | 124450 | 8/1995 |
| AU | 127863 | 9/1996 |
| FR | 1185637 | 8/1959 |

OTHER PUBLICATIONS

Solarshields Advertisement in Parade Magazine, Washington Post, May 10, 1992.

(List continued on next page.)

*Primary Examiner*—Peter Nerbun

(57) ABSTRACT

An apparatus for shielding a human eye of a patient while allowing the human eye contact with the air. A lens of the apparatus is fashioned to one or both of the eyes and is optically clear and optically correct in that it does not distort the patient's vision. The optically correct aspect of the lens is achieved by either polishing a mold for the lens or alternatively, by die-cutting the lens from an optically correct material. The lens may be held in place by an adjustable strap. A plurality of vents to allow the eye contact with the air are a plurality of apertures in the lens or a plurality of spaces or holes in a cushioning structure, where the cushioning structure is coupled to the perimeter of the surface of the lens facing the eye.

7 Claims, 13 Drawing Sheets

U.S. PATENT DOCUMENTS

| | | | | |
|---|---|---|---|---|
| D204,498 S | 4/1966 | Mitchell | .......................... | D57/1 |
| D204,816 S | 5/1966 | Boxer | .......................... | D57/1 |
| D205,246 S | 7/1966 | Mitchell | .......................... | D57/1 |
| D210,423 S | 3/1968 | Mitchell | .......................... | D57/1 |
| 3,395,406 A | 8/1968 | Smith | .......................... | 2/14 |
| D212,198 S | 9/1968 | Bloch | .......................... | D57/1 |
| D220,291 S | 3/1971 | Bloch | .......................... | D57/1 |
| 3,675,991 A | 7/1972 | Brenn | .......................... | 351/41 |
| D235,164 S | 5/1975 | Shindler | .......................... | D57/1 A |
| 3,901,589 A | 8/1975 | Bienenfeld | .......................... | 351/47 |
| 3,932,031 A | 1/1976 | Johnston | .......................... | 351/47 |
| 4,217,037 A | 8/1980 | Lemelson | .......................... | 351/44 |
| 4,298,991 A | 11/1981 | Recenello | .......................... | 2/13 |
| D270,165 S | 8/1983 | Burns | .......................... | D16/117 |
| D274,437 S | 6/1984 | Dianitsch | .......................... | D16/110 |
| D279,904 S | 7/1985 | Pulie | .......................... | D16/102 |
| 4,582,401 A | 4/1986 | Grindle | .......................... | 351/45 |
| D284,769 S | 7/1986 | MacWilliamson | .......................... | D16/118 |
| D285,020 S | 8/1986 | Schmidthaler | .......................... | D2/234 |
| 4,670,914 A | 6/1987 | Harris | .......................... | 2/436 |
| 4,701,962 A | 10/1987 | Simon | .......................... | 2/15 |
| 4,707,863 A * | 11/1987 | McNeal | .......................... | 2/436 |
| D293,328 S | 12/1987 | Murphy et al. | .......................... | D14/102 |
| D293,450 S | 12/1987 | Jannard | .......................... | D16/102 |
| 4,726,075 A | 2/1988 | Hinrichs | .......................... | 2/13 |
| D294,833 S | 3/1988 | Holden | .......................... | D16/112 |
| D295,286 S | 4/1988 | Takeuchi | .......................... | D16/110 |
| D295,533 S | 5/1988 | Wichers | .......................... | D16/102 |
| D295,870 S | 5/1988 | Laterre | .......................... | D16/112 |
| 4,741,611 A | 5/1988 | Burns | .......................... | 351/44 |
| 4,751,746 A | 6/1988 | Rustin | .......................... | 2/13 |
| 4,797,956 A | 1/1989 | Boyce | .......................... | 2/431 |
| 4,810,080 A | 3/1989 | Grendol et al. | .......................... | 351/41 |
| 4,877,320 A | 10/1989 | Holden | .......................... | 351/44 |
| D308,980 S | 7/1990 | McGee | .......................... | D16/112 |
| 4,955,708 A | 9/1990 | Kahaney | .......................... | 351/44 |
| D313,236 S | 12/1990 | Mackay | .......................... | D16/102 |
| 4,976,530 A | 12/1990 | Mackay et al. | .......................... | 351/44 |
| 5,000,558 A | 3/1991 | Blackstone | .......................... | 351/41 |
| D317,771 S | 6/1991 | Mackay | .......................... | D16/102 |
| D323,335 S | 1/1992 | Dalloz | .......................... | D16/112 |
| D323,515 S | 1/1992 | Arbez | .......................... | D16/102 |
| D324,394 S | 3/1992 | Jannard | .......................... | D16/102 |
| D329,445 S | 9/1992 | Jannard | .......................... | D16/116 |
| 5,146,623 A | 9/1992 | Paysan et al. | .......................... | 2/12 |
| D330,716 S | 11/1992 | Jannard | .......................... | D16/116 |
| D330,903 S | 11/1992 | Jannard | .......................... | D16/116 |
| 5,164,749 A | 11/1992 | Shelton | .......................... | 351/47 |
| D335,133 S | 4/1993 | Langley | .......................... | D16/102 |
| D335,135 S | 4/1993 | Bolle | .......................... | D16/112 |
| 5,218,385 A | 6/1993 | Lii | .......................... | 351/158 |
| 5,220,689 A | 6/1993 | Miller | .......................... | 2/12 |
| D339,596 S | 9/1993 | Kopfer | .......................... | D16/102 |
| 5,245,709 A * | 9/1993 | Shipcott | .......................... | 2/426 |
| 5,264,875 A | 11/1993 | Cooper | .......................... | 351/44 |
| D344,742 S | 3/1994 | Jannard | .......................... | D16/102 |
| 5,300,963 A | 4/1994 | Tanaka | .......................... | 351/44 |
| D347,015 S | 5/1994 | Saik | .......................... | D16/112 |
| 5,319,396 A | 6/1994 | Cesarczyk | .......................... | 351/62 |
| 5,321,443 A | 6/1994 | Huber et al. | .......................... | 351/47 |
| 5,357,292 A | 10/1994 | Wiedner | .......................... | 351/105 |
| 5,367,347 A * | 11/1994 | Wilson et al. | .......................... | 351/156 |
| D354,972 S | 1/1995 | Hirschman | .......................... | D16/314 |
| 5,379,464 A | 1/1995 | Schleger et al. | .......................... | 2/431 |
| 5,388,269 A | 2/1995 | Griffin | .......................... | 2/13 |
| 5,394,567 A | 3/1995 | Vatterott | .......................... | 2/449 |
| 5,402,189 A | 3/1995 | Gill | .......................... | 351/44 |
| 5,422,684 A | 6/1995 | Keller | .......................... | 351/41 |
| 5,423,092 A | 6/1995 | Kawai | .......................... | 2/441 |
| 5,428,407 A | 6/1995 | Sheffield | .......................... | 351/58 |
| 5,438,706 A | 8/1995 | Lambur | .......................... | 2/13 |
| 5,463,428 A | 10/1995 | Lipton et al. | .......................... | 351/158 |
| 5,469,229 A | 11/1995 | Greenbaum | .......................... | 351/44 |
| D365,357 S | 12/1995 | Jannard et al. | .......................... | D16/335 |
| D365,837 S | 1/1996 | Canavan | .......................... | D16/325 |
| D366,056 S | 1/1996 | Wolfe | .......................... | D16/314 |
| 5,483,303 A | 1/1996 | Hirschmann | .......................... | 351/118 |
| 5,488,438 A | 1/1996 | Cochran | .......................... | 351/45 |
| 5,502,515 A | 3/1996 | Sansalone | .......................... | 351/43 |
| 5,530,490 A | 6/1996 | Canavan | .......................... | 351/41 |
| D371,382 S | 7/1996 | Berthet-Bondet | .......................... | D16/326 |
| D371,384 S | 7/1996 | Bonnemere | .......................... | D16/330 |
| 5,543,864 A | 8/1996 | Hirschman et al. | .......................... | 351/47 |
| 5,548,351 A | 8/1996 | Hirschman et al. | .......................... | 351/47 |
| D374,025 S | 9/1996 | Canavan | .......................... | D16/330 |
| 5,561,480 A | 10/1996 | Capes | .......................... | 351/45 |
| D376,613 S | 12/1996 | Stepan et al. | .......................... | D16/327 |
| 5,598,230 A | 1/1997 | Quaresima | .......................... | 351/44 |
| D377,802 S | 2/1997 | Leonardi | .......................... | D16/313 |
| 5,608,469 A | 3/1997 | Bollé | .......................... | 351/44 |
| 5,614,963 A | 3/1997 | Parker | .......................... | 351/47 |
| 5,619,750 A | 4/1997 | Allewalt | .......................... | 2/13 |
| D379,633 S | 6/1997 | Garneau | .......................... | D16/315 |
| D380,003 S | 6/1997 | Wiedner | .......................... | D16/325 |
| 5,638,145 A * | 6/1997 | Jannard et al. | .......................... | 2/435 X |
| 5,654,786 A | 8/1997 | Bylander | .......................... | 351/49 |
| D385,897 S | 11/1997 | Lin | .......................... | D16/314 |
| D387,083 S | 12/1997 | Stables | .......................... | D16/321 |
| D388,453 S | 12/1997 | Lin | .......................... | D16/315 |
| D389,167 S | 1/1998 | Bolle | .......................... | D16/315 |
| D389,852 S | 1/1998 | Mage | .......................... | D16/321 |
| 5,710,613 A * | 1/1998 | Hughes | .......................... | 351/45 |
| D392,307 S | 3/1998 | Wilson | .......................... | D16/326 |
| D396,484 S | 7/1998 | Stables | .......................... | D16/326 |
| D397,132 S | 8/1998 | Yee | .......................... | D16/315 |
| D397,354 S | 8/1998 | Kuo | .......................... | D16/330 |
| D397,713 S | 9/1998 | Brune et al. | .......................... | D16/326 |
| D398,021 S | 9/1998 | Bolle | .......................... | D16/315 |
| D398,323 S | 9/1998 | Bolle | .......................... | D16/315 |
| D399,519 S | 10/1998 | Yee | .......................... | D16/314 |
| D401,607 S | 11/1998 | Miniutti | .......................... | D16/314 |
| D402,303 S | 12/1998 | Simioni | .......................... | D16/326 |
| D403,345 S | 12/1998 | Flanagan | .......................... | D16/327 |
| D404,054 S | 1/1999 | Arnette et al. | .......................... | D16/326 |
| D404,416 S | 1/1999 | Wiedner | .......................... | D16/315 |
| D405,816 S | 2/1999 | Crestin-Billet | .......................... | D16/315 |
| D406,858 S | 3/1999 | Arnette | .......................... | D16/326 |
| D407,566 S | 4/1999 | Lane | .......................... | D16/326 |
| D408,840 S | 4/1999 | Lane | .......................... | D16/321 |
| D410,022 S | 5/1999 | Conway | .......................... | D16/327 |
| D416,933 S | 11/1999 | Lane | .......................... | D16/326 |
| D417,461 S | 12/1999 | Lane | .......................... | D16/326 |
| D418,534 S | 1/2000 | Lane | .......................... | D16/326 |
| D419,585 S | 1/2000 | Lane | .......................... | D16/325 |
| D422,007 S | 3/2000 | Pickering et al. | .......................... | D16/326 |
| D433,697 S | 11/2000 | Lane | .......................... | D16/315 |
| D433,698 S | 11/2000 | Lane | .......................... | D16/328 |
| D434,062 S | 11/2000 | Lane | .......................... | D16/326 |
| D434,063 S | 11/2000 | Lane | .......................... | D16/326 |
| D434,064 S | 11/2000 | Lane | .......................... | D16/330 |
| D434,789 S | 12/2000 | Lane | .......................... | D16/326 |
| D435,579 S | 12/2000 | Lane | .......................... | D16/327 |
| 6,196,681 B1 | 3/2001 | Canavan | .......................... | 351/106 |
| D445,442 S | 7/2001 | Lee | .......................... | D16/315 |

OTHER PUBLICATIONS

Bollé Polarisant Collection, 1993 Catalog.

Fisherman Eyewear, 1996 Catalog.

Fisherman Eyewear, 1997 Catalog.

Costa Del Mar, 1997 Catalog.
Hobie Polarized Sunglasses, 1997 Catalog.
Ocean Waves Advertisement, no date.
USA Sport Advertisement for Adjustable Deluxe Series, no date.

Vision Works, p. 21, 1990 Catalog.
Giorgio Armani, p. 13, 1995 Catalog.
Guild Guide, p. 9, 1972 Catalog.

* cited by examiner

OPTICALLY CORRECT AND CLEAR EYESHIELDS

This is a divisional of U.S. patent application Ser. No. 09/852,406, filed May 9, 2001, the contents of which are hereby incorporated by reference.

RELATED APPLICATIONS

This patent application claims priority under 35 U.S.C. §120 and is a continuation in part of the co-pending U.S. design application Ser. No. 29/130,115 filed on Sep. 26, 2000, U.S. Pat. No. D462,374 and entitled "EYE-SHIELDS." The design application 29/130,115 filed on Sep. 26, 2000 and entitled "EYESHIELDS" is also hereby incorporated by reference. This application also claims priority under 35 U.S.C. §120 and is a continuation in part of the co-pending U.S. design application 29/130,173 filed on Sep. 27, 2000 U.S. Pat. No. D457,908 and entitled "EYE-SHIELDS." The design application 29/130,173 filed on Sep. 27, 2000 and entitled "EYESHIELDS" is also hereby incorporated by reference.

FIELD OF THE INVENTION

The invention relates to the field of medical eyeshields. More particularly, the invention relates to the field of designing and manufacturing medical eyeshields with optically correct and optically clear lenses.

BACKGROUND OF THE INVENTION

Physicians perform various eye surgeries daily, each requiring specific types of care. Many times, after one of these surgeries, as part of the rehabilitation process, the patient is required to shield the eye from the environment as to not hinder the healing process. Additionally, many of these patients are able to maintain normal vision while the eye heals. Such operations include cataract surgery and the ever increasingly popular vision correction surgeries. Because a patient of one of these surgeries regains normal vision immediately or shortly after the operation is completed, an optically clear and correct eyeshield is needed so that the patient may perform everyday tasks while the eye heals. It is also important that the eye receives adequate air circulation during the healing process.

Existing eyeshields do not provide the patient with all of the necessary aforementioned aspects. Prior eyeshield designs lack a functional eyeshield that also allows for comfort and accurate vision. In other words, prior designs do embody an eyeshield that allows for proper air circulation for optimal healing capabilities combined with a comfortable fit and optically correct vision.

Absent in the prior art is a design encompassing all of the aspects necessary to effectively and efficiently heal the eye while allowing the patient normal vision through an optically correct lens. A design such as this is needed to allow a patient to quickly heal from a surgery without losing the ability to perform everyday functions.

SUMMARY OF THE INVENTION

The present invention is an apparatus for shielding a human eye while allowing air to circulate to the eye. The present invention is an eyeshield which includes an optically correct viewing area and a plurality of vents. The eyeshield can be held in place with tape, or adhesive or can include an adjustable strap for holding the eyeshield and the optically correct viewing area in place in front of the user's eye. The eyeshield of the present invention includes one surface that faces the eye and one surface that faces away from the eye.

The eyeshield in the present invention is optically clear as well as optically correct in that it does not distort the user's vision. This is achieved by two different methods. The preferred method utilizes a polished mold to achieve an optically correct surface while another method to achieve an optically correct eyeshield utilized by the present invention is to die cut the lens from an optically correct material.

The present invention may be fashioned to protect one or both eyes. In both cases, the plurality of vents are actually a plurality of apertures. The preferred embodiment includes apertures in the form of slots while an alternate embodiment includes apertures in the form of holes. In either case, the plurality of vents do not distort the patient's vision.

DETAILED DESCRIPTION OF A PREFERRED EMBODIMENT

FIGS. 1–5 depict the preferred embodiment of the present invention. Referring to the top view in FIG. 1, the eyeshield 10 is fashioned to cover one of the user's eyes, as well as the area around the eye. The bottom view is a mirror image of the top view. A plurality of vents 14 in the preferred embodiment of the present invention are slots which are arranged in a pattern so that the optically correct lens 12 is not interrupted in the viewing area in front of the eye, and therefore, do not distort the user's vision. The vents allow fresh air to impinge on the users eye, while keeping fingers, other objects and most dust away from the eye.

Figure 3:
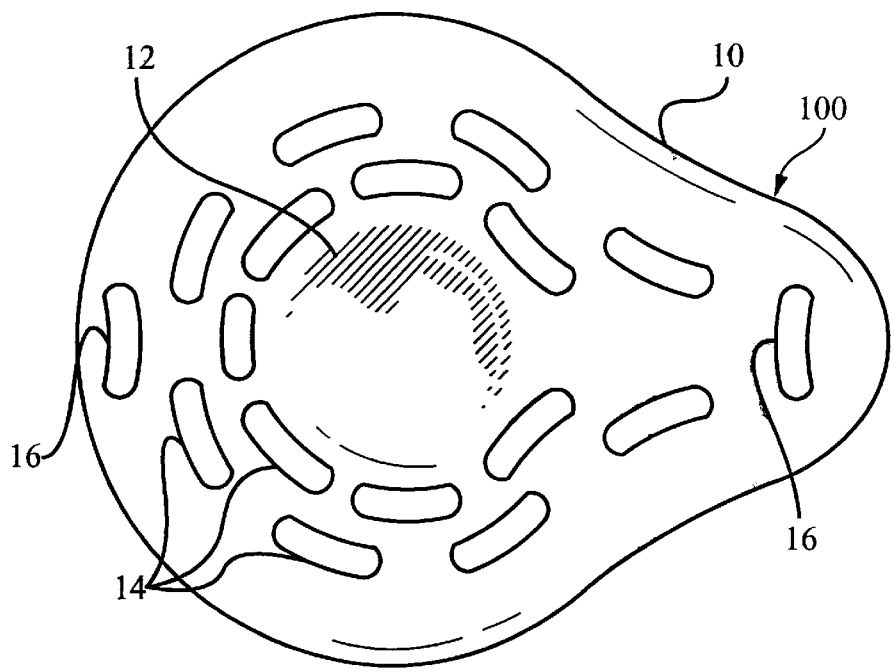
FIG. 3 illustrates a front elevation view of an optically correct eyeshield in accordance with the preferred embodiment of the present invention.
Figure 4:
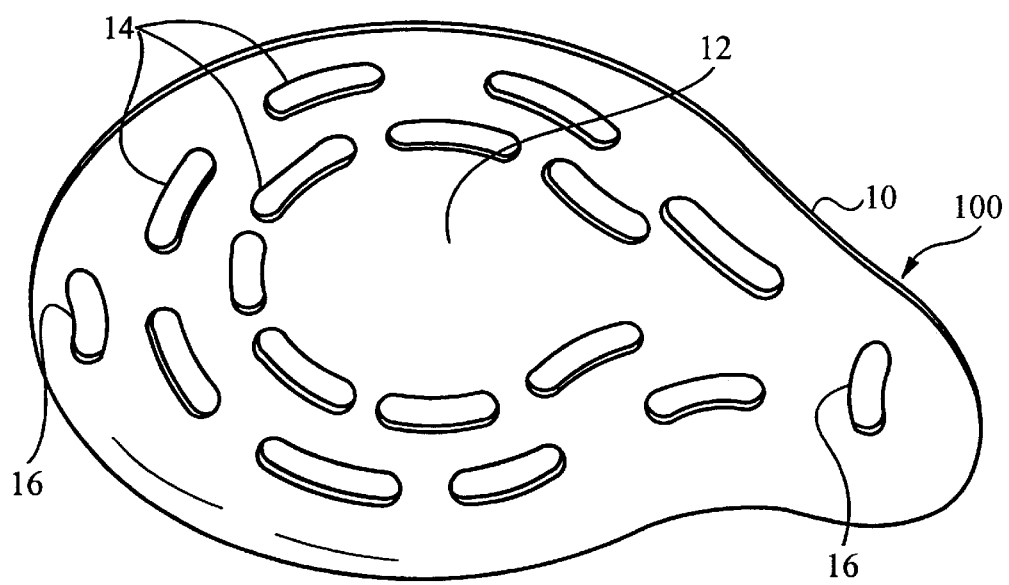
FIG. 4 illustrates a top perspective view of an optically correct eyeshield in accordance with the preferred embodiment of the present invention.
Figure 5:
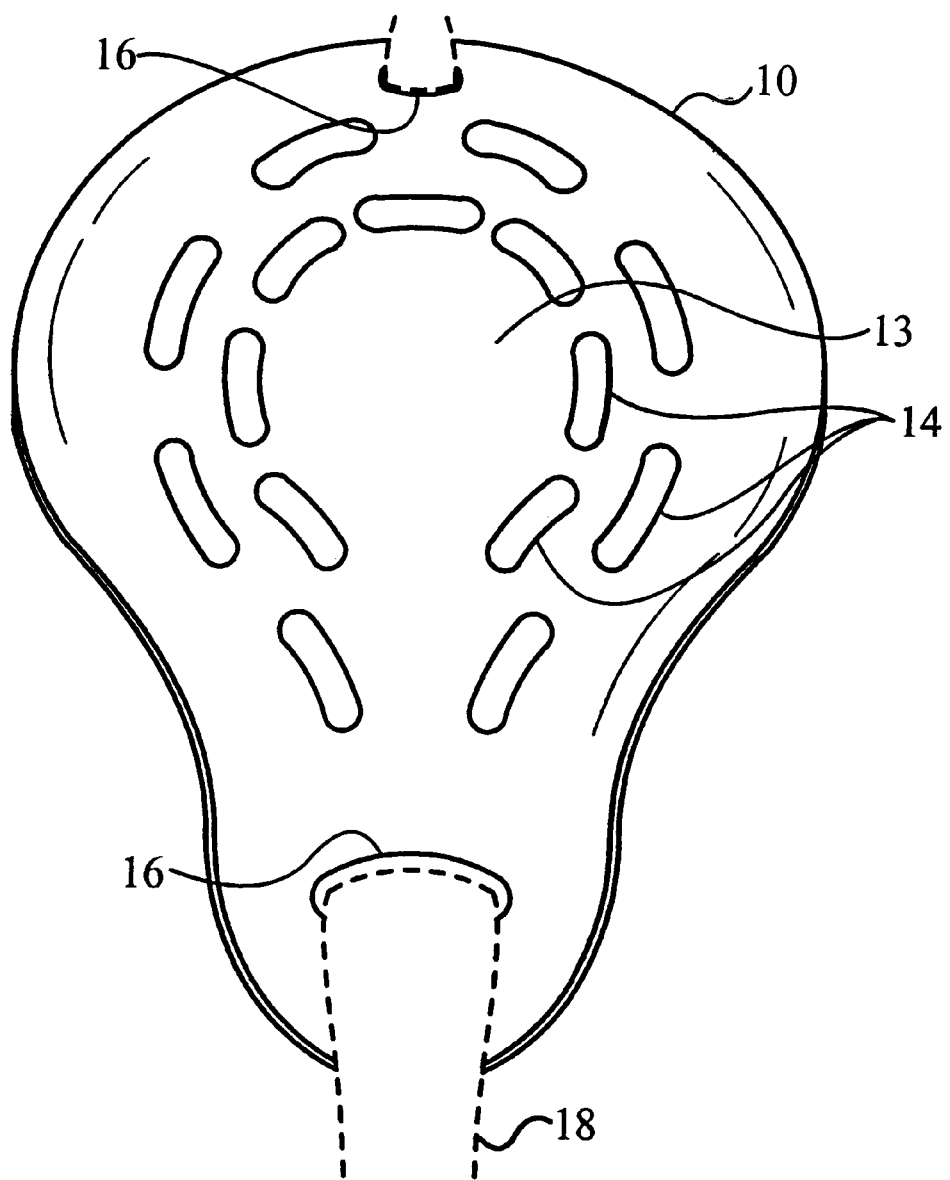
FIG. 5 illustrates a side perspective view of an optically correct eyeshield in accordance with the preferred embodiment of the present invention.

Referring to the front elevation view of the preferred embodiment in FIG. 3, the pattern of the plurality of vents 14 is displayed in a clearer fashion. It will be apparent to those of or ordinary skill in the art that other patterns are possible for the vents 14. However, to maintain the shield as optically correct it is desired that the vents 14 not be positioned in the viewing area of the eyeshield 10.

Figure 1:
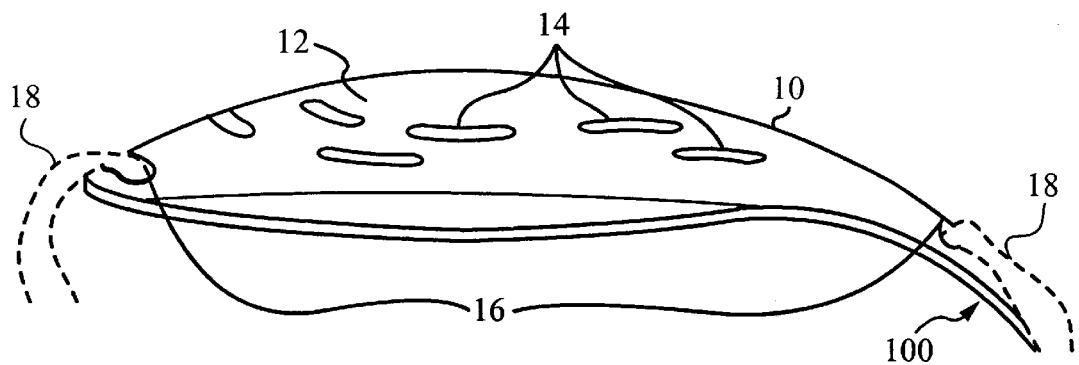
FIG. 1 illustrates a top view of an optically correct eyeshield in accordance with the preferred embodiment of the present invention.
Figure 2:
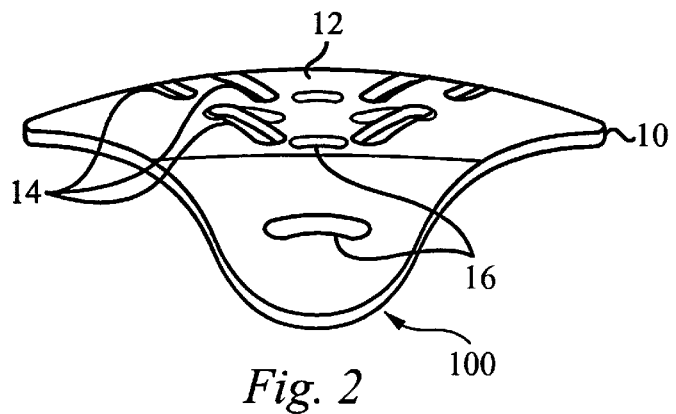
FIG. 2 illustrates a side view of an optically correct eyeshield in accordance with the preferred embodiment of the present invention.

Referring again to the preferred embodiment depicted in FIG. 1, the set of openings 16 allow the strap 18 to be coupled with the eyeshield 10. The strap 18 is adjustable in that it is made of an elastic material. Alternative embodiments of the strap 18 can utilize adjusting devices coupled with an elastic strap 18, or a combination thereof Alternatively, the eyeshield 10 can be affixed to the user's face over their eye using adhesive tape or another adhesive. In such a circumstance, the openings 16 and the strap 18 need not be present.

The slope of the eyeshield 10 is adopted to make contact along its periphery with the average user's face. This contact serves to prevent dust and other irritants from access to the interior of the eyeshield 10 along its periphery and hence the eye. The eyeshield 10 is substantially circular. The eyeshield 10 includes a nose bridge protrusion 100. The nose bridge protrusion 100 is adopted to ride on and above the user's nose such that the increase in dimension of the eyeshield 10 toward its substantially circular region maintains close proximity to the typical user's nose and eyebrow. The eyeshield 10 and the nose bridge protrusion 100 can be manufactured in several sizes to accomodate an even wider range of users.

According to the preferred embodiment depicted in FIGS. 1–5, the eyeshield 10 is produced from a mold. To achieve the optically correct lens 12 from the mold, the mold is preferably polished.

Figure 6:
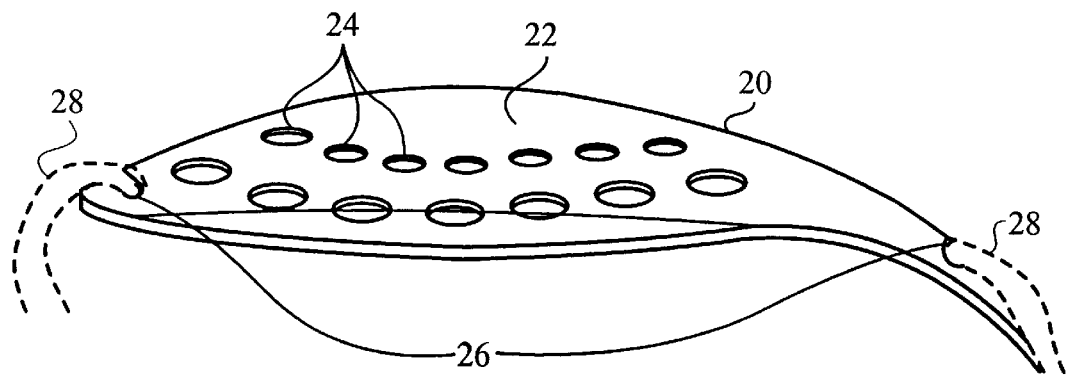
FIG. 6 illustrates a top view of an optically correct eyeshield in accordance with an alternative embodiment of the present invention.
Figure 7:
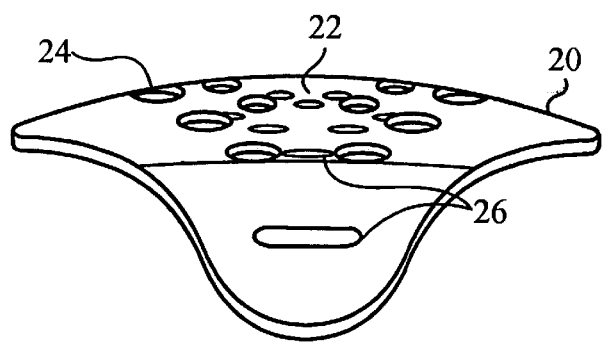
FIG. 7 illustrates a side view of an optically correct eyeshield in accordance with an alternative embodiment of the present invention.
Figure 8:
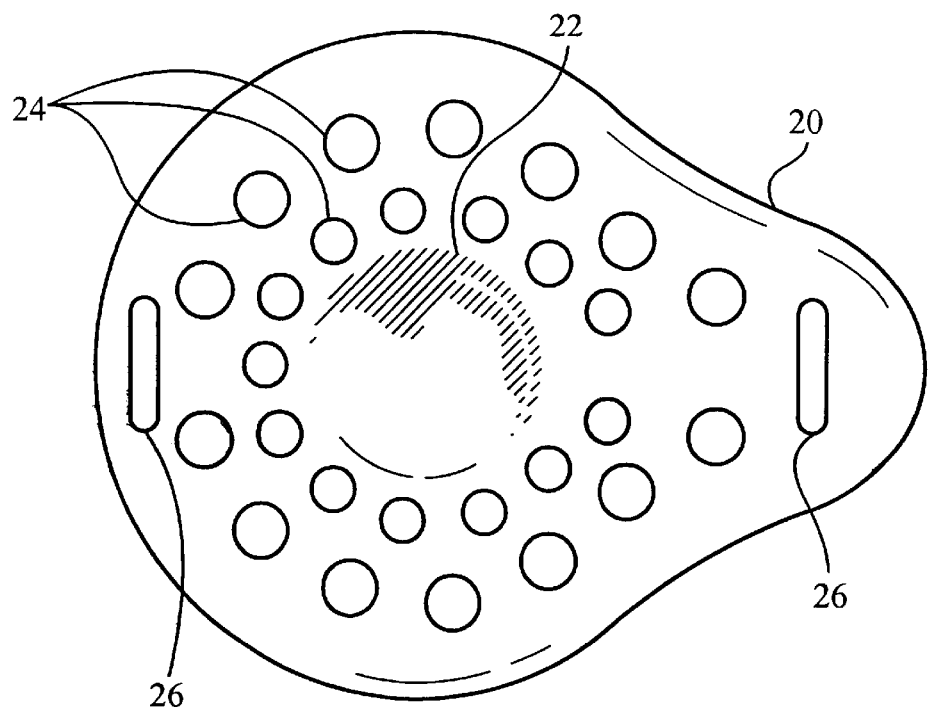
FIG. 8 illustrates a front elevation view of an optically correct eyeshield in accordance with an alternative embodiment of the present invention.
Figure 9:
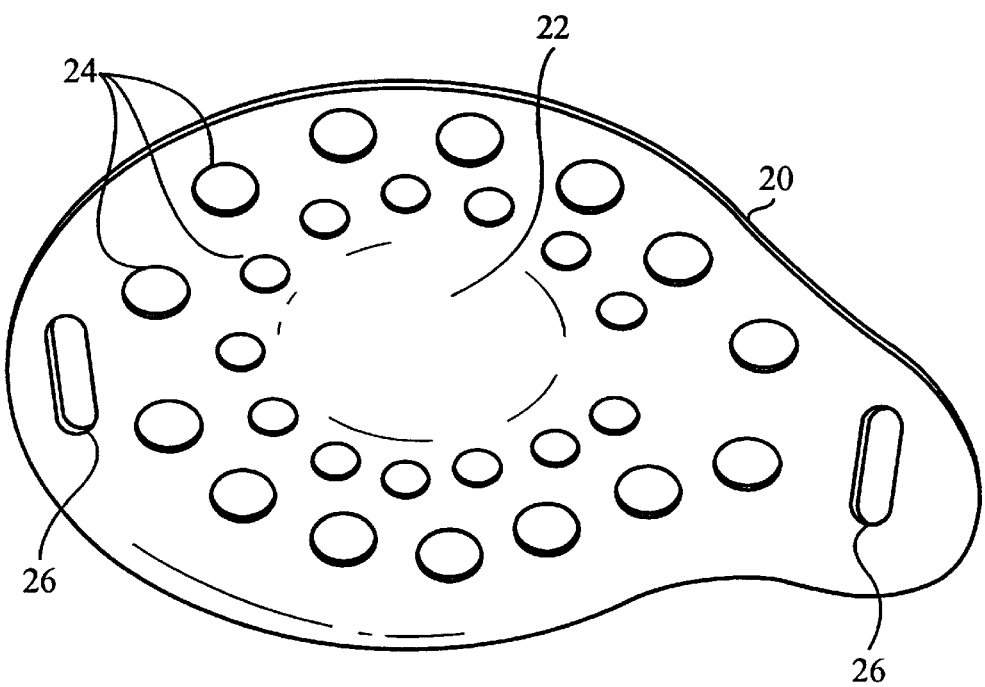
FIG. 9 illustrates a top perspective view of an optically correct eyeshield in accordance with an alternative embodiment of the present invention.
Figure 10:
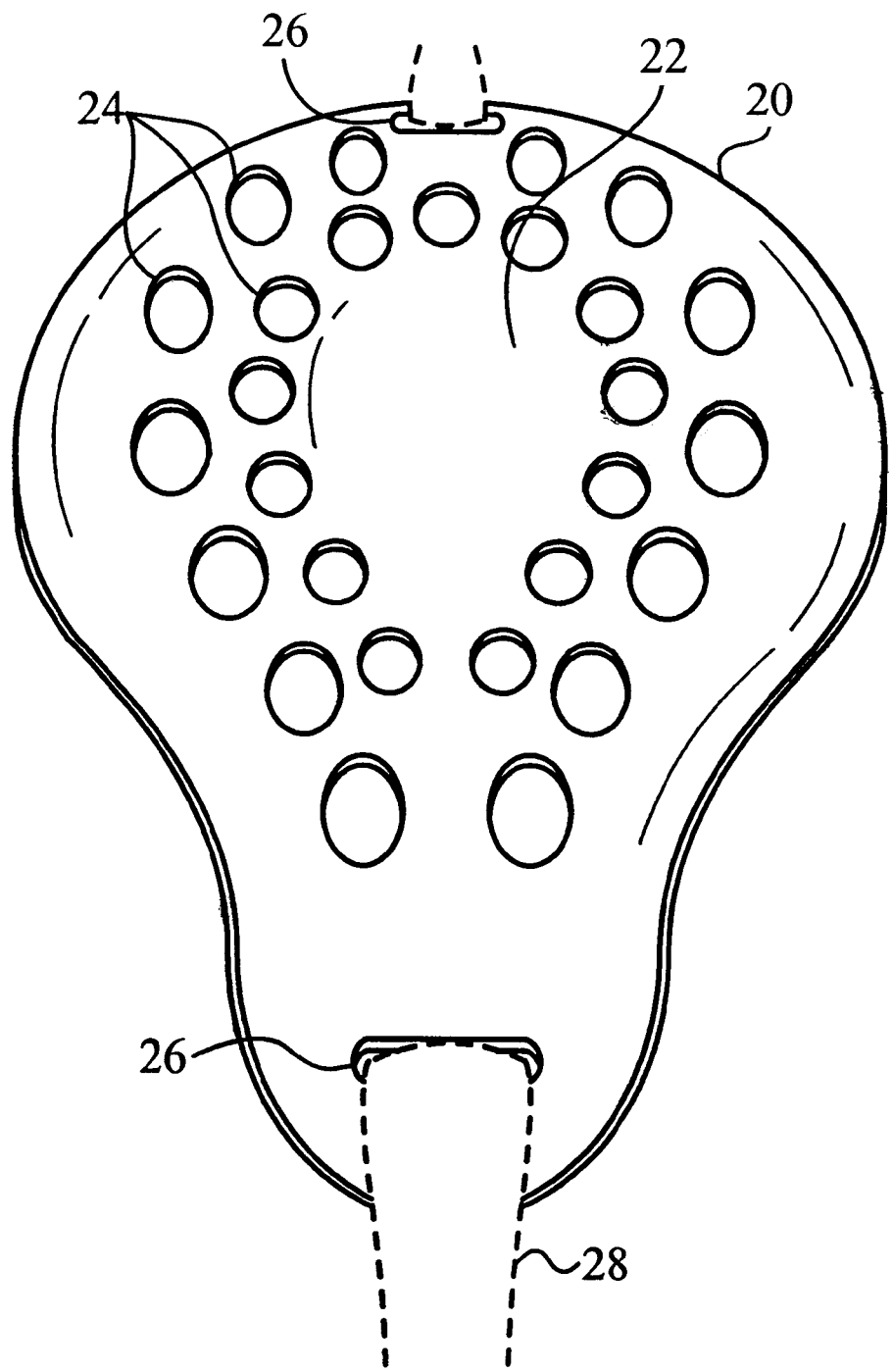
FIG. 10 illustrates a side perspective view of an optically correct eyeshield in accordance with an alternative embodiment of the present invention.

FIGS. 6–10 depict a first alternative embodiment of the present invention. Referring to FIG. 6, the eyeshield 20 is again fashioned to cover one of the patient's eyes as well as the area around the eye. However, the plurality of vents 24 in this case are holes. Similar to the slots of the preferred embodiment, the holes are arranged in a pattern so that the optically correct lens 22 is not interrupted in the viewing area in front of the eye, and therefore, is incapable of distorting the user's vision. Referring to the front elevation view of the first alternative embodiment in FIG. 8, the pattern of the plurality of vents 24 is displayed in a clearer fashion. Also in the first alternative embodiment depicted in FIG. 6, the set of openings 26 allows the strap 28 to be coupled with the eyeshield 20. The strap 28 is also adjustable in the first alternative embodiment in that it is made of an elastic material. Alternative embodiments of the strap 28 can utilize adjusting devices coupled with an elastic strap 28, or a combination thereof.

Again, similar to the preferred embodiment depicted in FIGS. 1–5, the eyeshield 20 depicted in FIGS. 6–10 is produced from a mold. In order to achieve the optically correct lens 22 from the mold, the mold must be polished.

Figure 11:
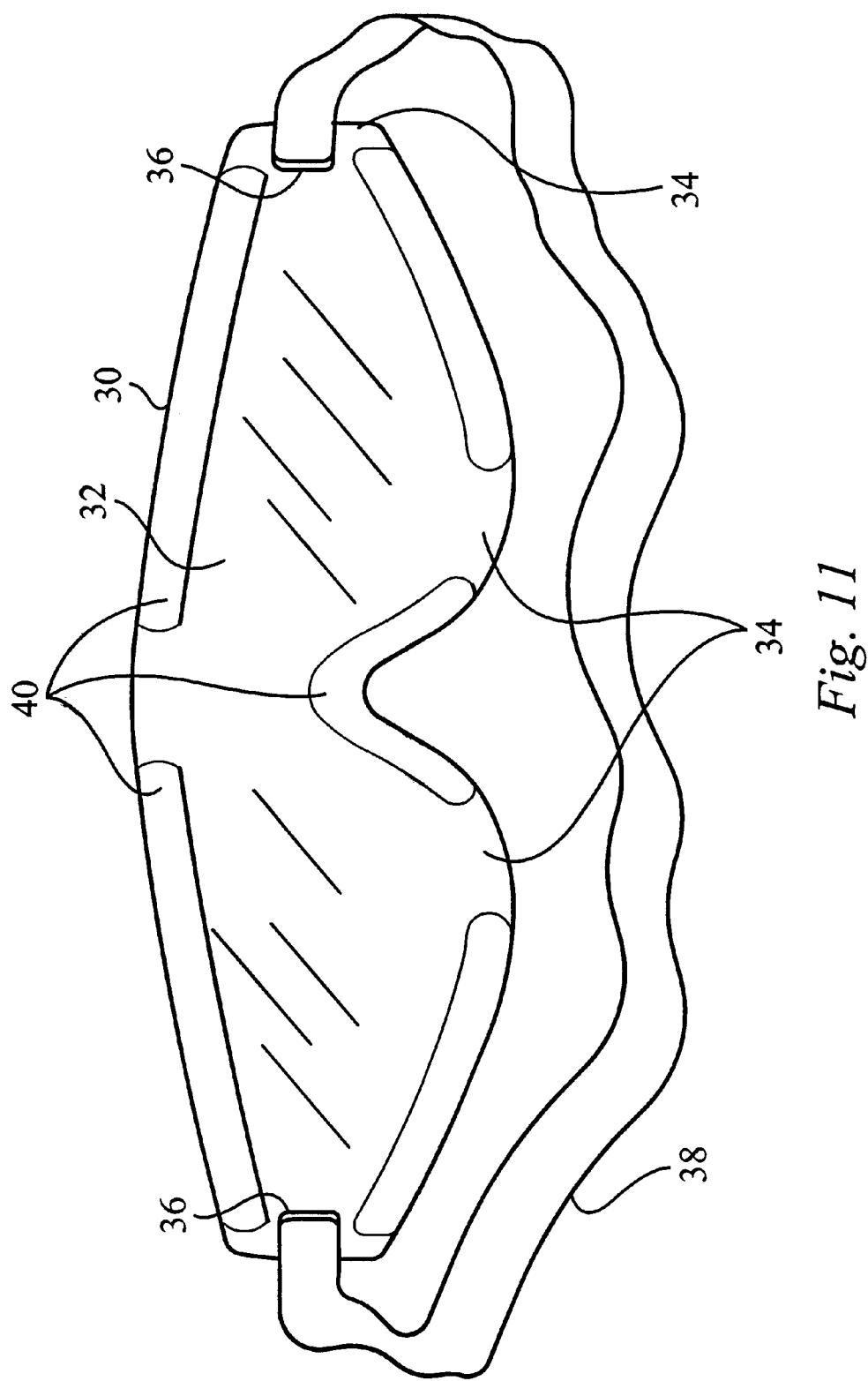
FIG. 11 illustrates a front elevation view of an optically correct eyeshield for two eyes in accordance with an alternative embodiment of the present invention.
Figure 12:
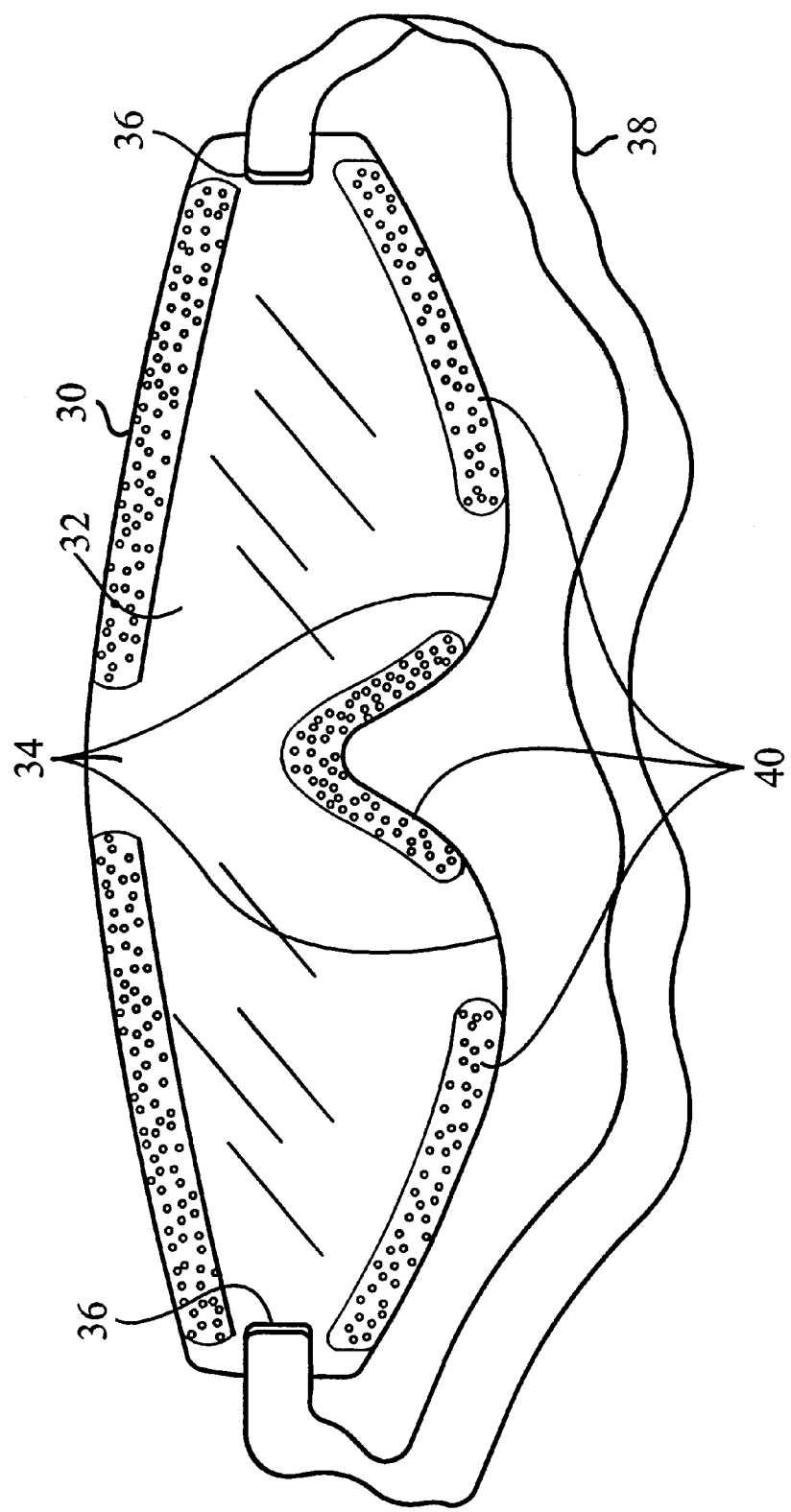
FIG. 12 illustrates a rear elevation view of an optically correct eyeshield for two eyes in accordance with an alternative embodiment of the present invention.
Figure 13A:
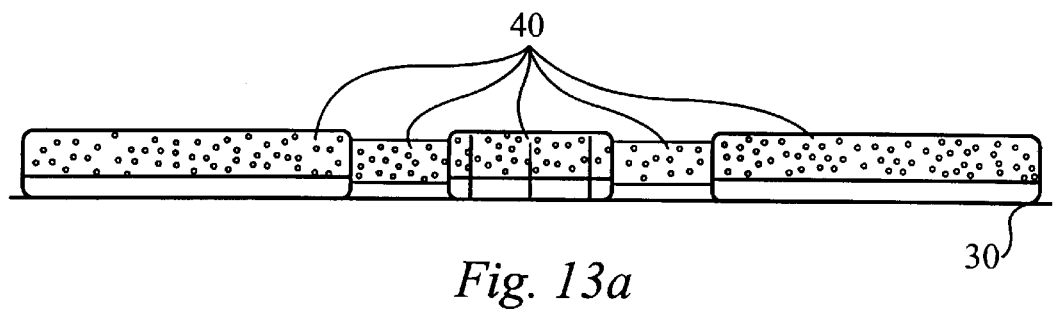
FIG. 13a illustrates a bottom view of an optically correct eyeshield for two eyes in accordance with an alternative embodiment of the present invention.
Figure 13B:
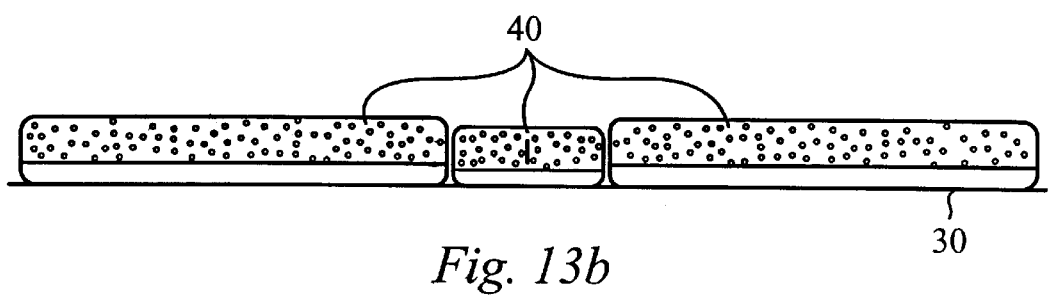
FIG. 13b illustrates a top view of an optically correct eyeshield for two eyes in accordance with an alternative embodiment of the present invention.
Figure 13C:
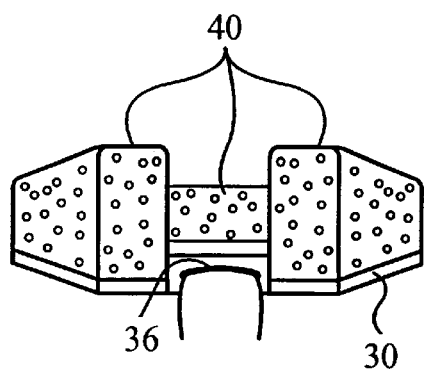
FIGS. 13c & 13d illustrate side views of an optically correct eyeshield for two eyes in accordance with an alternative embodiment of the present invention.
Figure 13D:
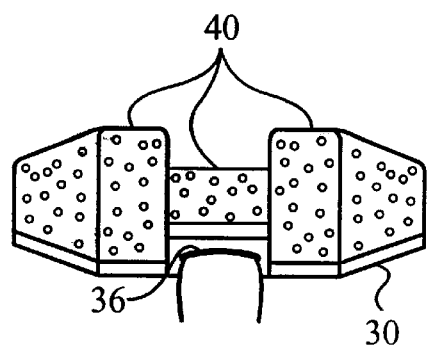
Figure 14:
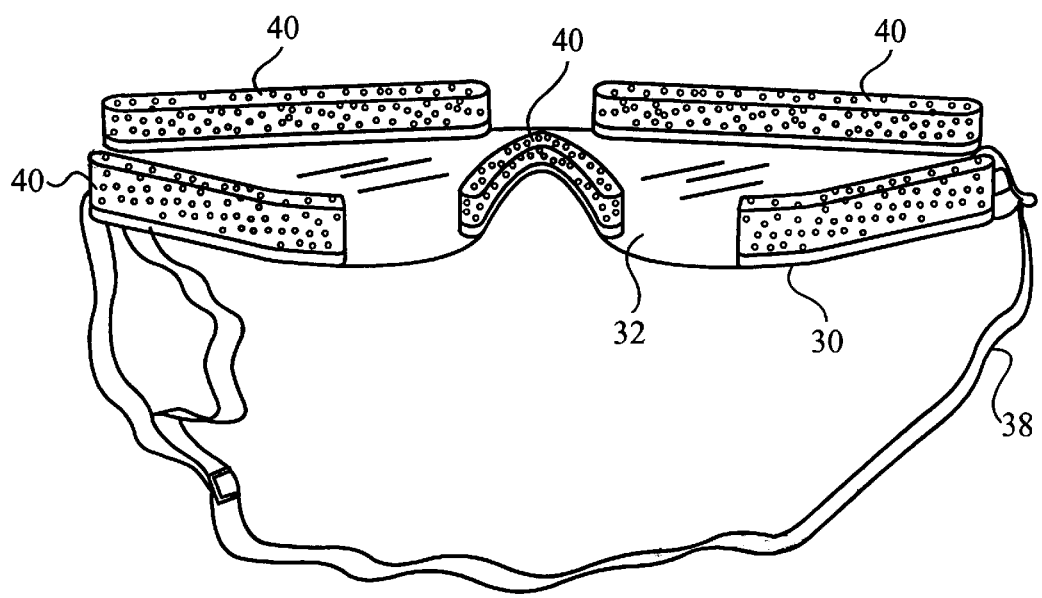
FIG. 14 illustrates a bottom perspective view of an optically correct eyeshield for two eyes in accordance with an alternative embodiment of the present invention.
Figure 15:
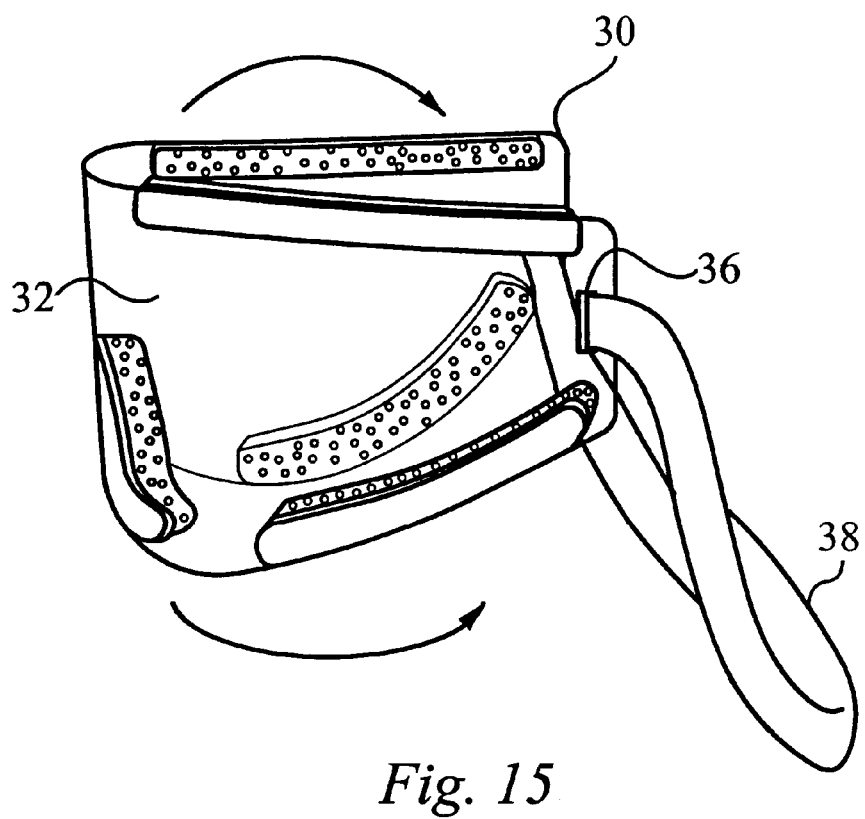
FIGS. 15 & 16 illustrate a side perspective view of an optically correct eyeshield for two eyes in accordance with an alternative embodiment of the present invention.
Figure 16:
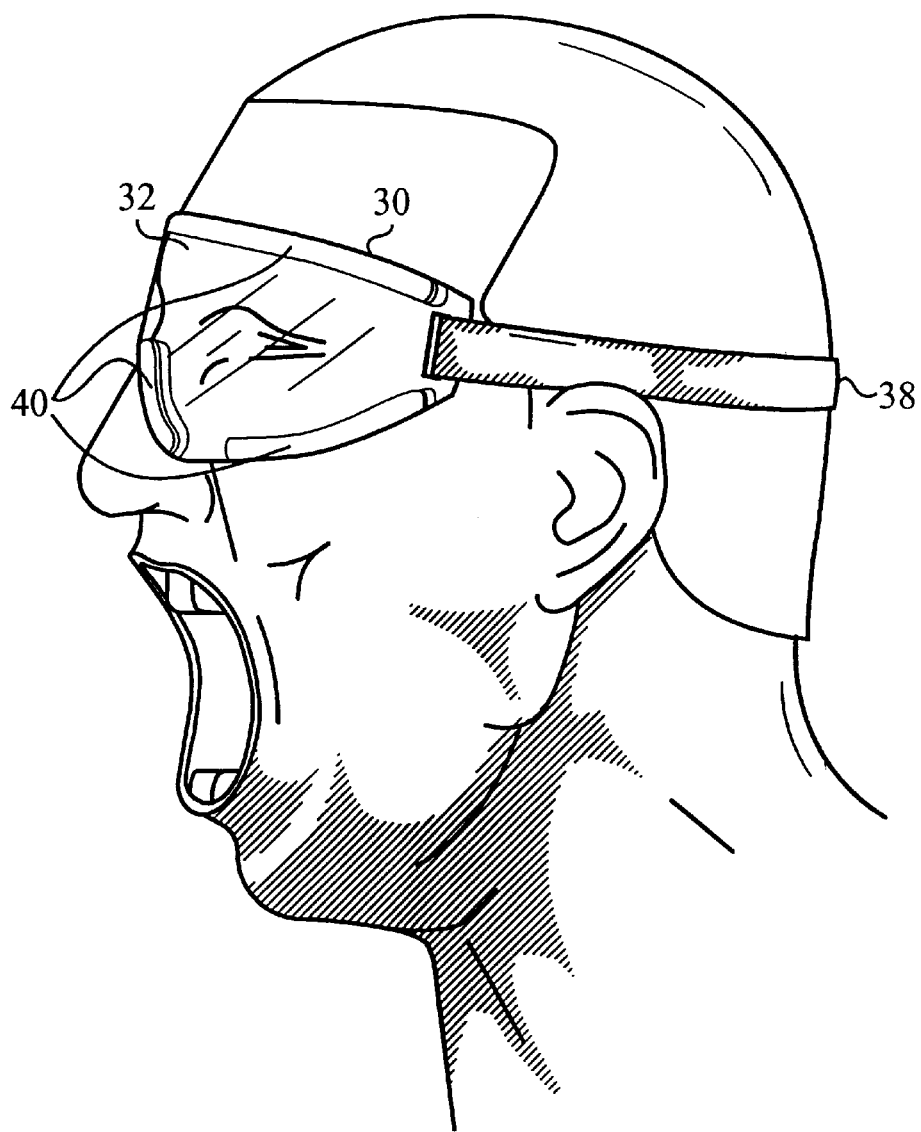
Figure 17:
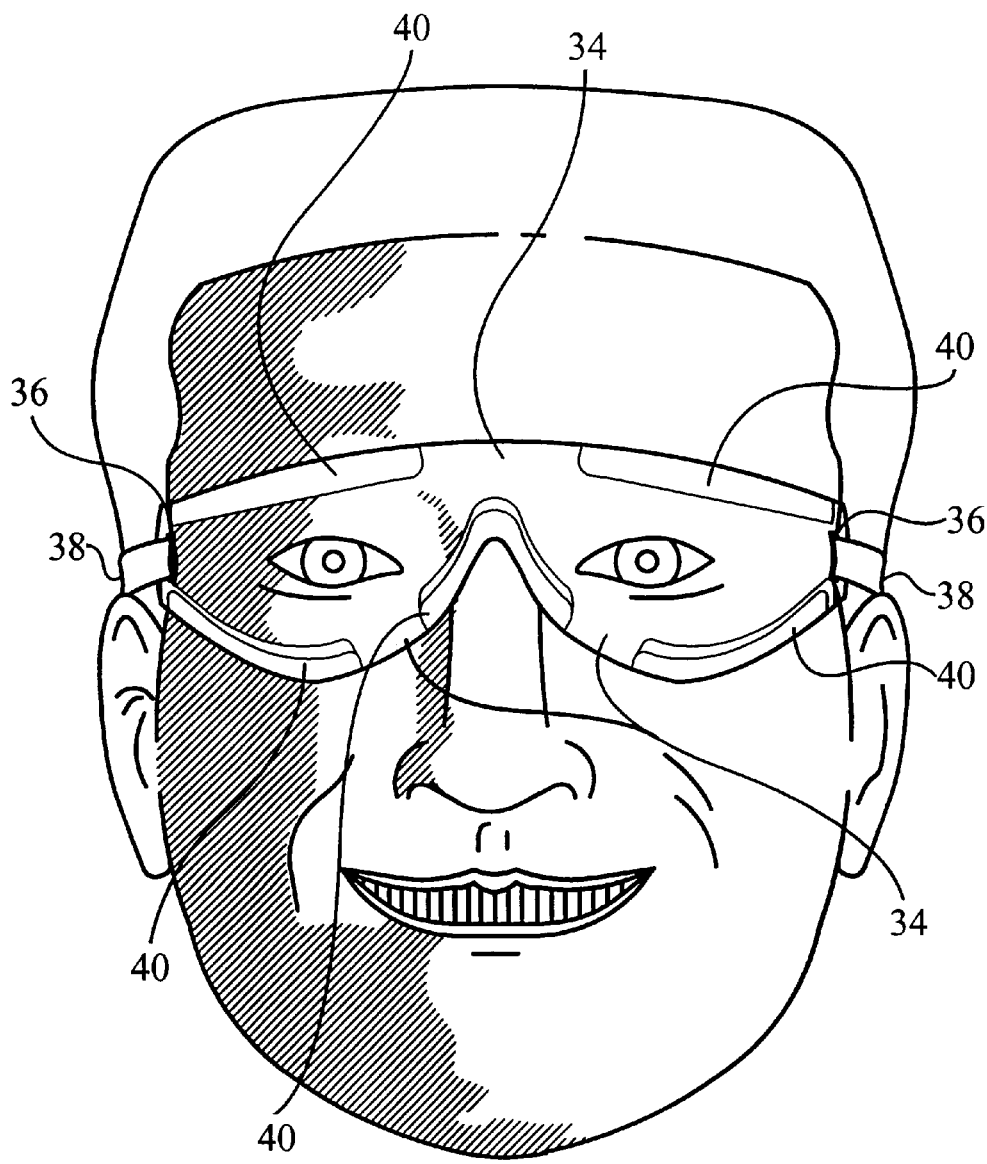
FIG. 17 illustrates a front perspective view of an optically correct eyeshield for two eyes in accordance with an alternative embodiment of the present invention.

FIGS. 11–17 depict a second alternative embodiment of the present invention. Referring to FIG. 11, the optically correct lens 32 of the eyeshield 30 in this case is fashioned to provide protection for both eyes as well as the area of the face surrounding the eyes. In embodiments such as the second alternative embodiment in FIG. 11, the optically correct lens 32 is die-cut from an optically correct material.

A cushioning structure 40 outlines the perimeter of the optically correct lens 32 on the surface facing the eye. In this second alternative embodiment, the plurality of vents 34 are formed by the spaces formed in the cushioning structure 40. Other embodiments will include a cushioning structure 40 fashioned as one continuous piece outlining the perimeter of the optically correct lens 32. In such an embodiment, a plurality of vents are formed by holes in the cushioning structure 40.

Again referring to the second alternative embodiment in FIG. 11, the set of openings 36 allow the strap 38 to be coupled with the eyeshield 30. The strap 38 is also adjustable in this second alternative embodiment in that it is made of an elastic material. Alternative embodiments of the strap 38 can utilize adjusting devices coupled with the strap 28, or a combination thereof.

The present invention has been described in terms of specific embodiments incorporating details to facilitate the understanding of the principles of construction and operation of the invention. Such reference herein to specific embodiments and details thereof is not intended to limit the scope of the claims appended hereto. For example, the application of the eyeshield of the present invention is not limited to eye surgery patients. It will be apparent to those skilled in the art that modifications may be made in the embodiment chosen for illustration without departing from the spirit and scope of the invention.

What is claimed is:

1. A method of manufacturing an eyeshield comprising the steps of:
   a. producing a mold that will fashion an eyeshield wherein the eyeshield is optically clear, and further wherein the eyeshield is fashioned to be worn over a single eye of a user; and
   b. polishing the surface of the mold to facilitate the eyeshield being optically correct.

2. The method as claimed in claim 1 further comprising coupling an adjustable strap with the eyeshield.

3. The method as claimed in claim 1 wherein the mold fashions the eyeshield including a plurality of vents.

4. The method as claimed in claim 3 wherein the plurality of vents are configured as to not distort vision.

5. A method of manufacturing an eyeshield comprising the steps of:

a. cutting an eyeshield from an optically clear and optically correct material;

b. affixing a noncontinuous cushioning structure having a plurality of vents to the perimeter of a first surface of the eyeshield such that when the eyeshield is worn by a user and pressure is applied to a second surface of the eyeshield, the cushioning structure prevents any portion of the first surface of the eyeshield from touching the user's face; and c. coupling an adjustable strap with the eyeshield.

6. A method of manufacturing an eyeshield comprising the steps of:

a. producing a mold that will fashion an eyeshield wherein the eyeshield is optically clear, and further wherein the eyeshield is fashioned to be worn over a single eye of a user; and b. polishing the surface of the mold to facilitate the eyeshield being optically correct, wherein the mold fashions the eyeshield including a plurality of vents configured as to not distort vision.

7. The method as claimed in claim 6 further comprising coupling an adjustable strap with the eyeshield.

* * * * *

UNITED STATES PATENT AND TRADEMARK OFFICE
CERTIFICATE OF CORRECTION

PATENT NO. : 6,609,255 B2
DATED : August 26, 2003
INVENTOR(S) : Henry Welling Lane et al.

It is certified that error appears in the above-identified patent and that said Letters Patent is hereby corrected as shown below:

Column 1,
Line 49, replace "embody an eyeshield" with -- not embody an eyeshield --

Signed and Sealed this

Twenty-first Day of June, 2005

JON W. DUDAS
*Director of the United States Patent and Trademark Office*